(12) United States Patent
Jarolem

(10) Patent No.: US 9,451,996 B2
(45) Date of Patent: Sep. 27, 2016

(54) FACET LAMINA PLATE SYSTEM

(71) Applicant: Thunder Road Properties, LP, Davie, FL (US)

(72) Inventor: Kenneth Jarolem, Davie, FL (US)

(*) Notice: Subject to any disclaimer, the term of this patent is extended or adjusted under 35 U.S.C. 154(b) by 118 days.

(21) Appl. No.: 13/826,984

(22) Filed: Mar. 14, 2013

(65) Prior Publication Data

US 2014/0277140 A1 Sep. 18, 2014

(51) Int. Cl.
*A61B 17/88* (2006.01)
*A61B 17/70* (2006.01)

(52) U.S. Cl.
CPC ................................ *A61B 17/7064* (2013.01)

(58) Field of Classification Search
CPC .......... A61B 17/7064; A61B 17/1757; A61B 17/1671; A61B 17/7067; A61B 17/7059; A61B 17/7062
USPC ................................ 606/246–299; 623/17.11
See application file for complete search history.

(56) References Cited

U.S. PATENT DOCUMENTS

| | | | | |
|---|---|---|---|---|
| 5,437,672 A | * | 8/1995 | Alleyne | .......................... 606/279 |
| 5,951,557 A | * | 9/1999 | Luter | ............................. 606/286 |
| 6,132,464 A | | 10/2000 | Martin | |
| 6,355,038 B1 | * | 3/2002 | Pisharodi | ....................... 606/300 |
| 6,974,478 B2 | | 12/2005 | Reiley et al. | |
| 7,537,604 B2 | * | 5/2009 | Huebner | ......................... 606/281 |
| 7,591,837 B2 | | 9/2009 | Goldsmith | |
| 7,635,365 B2 | * | 12/2009 | Ellis et al. | ....................... 606/71 |
| 7,837,711 B2 | | 11/2010 | Bruneau et al. | |
| 7,862,590 B2 | | 1/2011 | Lim et al. | |
| 8,163,017 B2 | | 4/2012 | Reiley | |
| 2005/0267579 A1 | | 12/2005 | Reiley et al. | |
| 2006/0264948 A1 | * | 11/2006 | Williams | ......................... 606/69 |
| 2007/0198091 A1 | | 8/2007 | Boyer et al. | |
| 2008/0051791 A1 | * | 2/2008 | Young et al. | .................... 606/69 |
| 2008/0132951 A1 | | 6/2008 | Reiley et al. | |
| 2008/0234735 A1 | | 9/2008 | Joshi | |
| 2010/0131008 A1 | | 5/2010 | Overes et al. | |
| 2010/0262193 A1 | * | 10/2010 | Frigg et al. | ................... 606/281 |
| 2011/0060366 A1 | | 3/2011 | Heim et al. | |

FOREIGN PATENT DOCUMENTS

WO       2010/122472 A1    10/2010

OTHER PUBLICATIONS http://facetsolutions.com/Articles09-11-06.html.

* cited by examiner

*Primary Examiner* — Mary Hoffman
*Assistant Examiner* — Tara R Carter
(74) *Attorney, Agent, or Firm* — Akerman LLP

(57) ABSTRACT

An apparatus for securing facet joints of a spine of a patient is provided. The apparatus may include a first connection device configured to be positioned directly through a first facet joint of the spine of the patient. Additionally, the apparatus may include a second connection device configured to be positioned directly through a second facet joint of the spine of the patient. Furthermore, the apparatus may include a plate configured to engage the first and second connection devices after the first and second connection devices are positioned through the first and second facet joints respectively. The plate may include a first slot configured to engage the first connection device and a second slot configured to engage the second connection device. The first slot may be perpendicular to the second slot, and the first slot may be perpendicular to a long axis of the spine of the patient.

8 Claims, 16 Drawing Sheets

FACET LAMINA PLATE SYSTEM

FIELD OF THE INVENTION

The present application relates to medical devices and instruments related to spine surgeries, and, more particularly, to a facet lamina plate system.

BACKGROUND

Over the years, substantial progress has been made in medical technology, medical devices, and surgical techniques. This progress has dramatically improved patient survival rates, life expectancies, and quality of living, while also, often times, simultaneously reducing the incidence of serious complications or side effects. Despite such progress, continuous improvements to such medical technology, medical devices, and surgical techniques are needed to provide physicians with the most effective and safe treatments and procedures that are utilized to treat patients. As an example, back surgeries such as spinal fusions, discectomies, foraminotomies, laminectomies, and spinal disc replacements, while often very useful in treating various back-related conditions, are typically quite invasive and may potentially have unwanted or unintended consequences. Such consequences may include, but are not limited to, failed back syndrome, pseudoarthrosis, implant failure, the migration or subsidence of grafts, infection, bleeding, nerve damage, continued back pain after surgery, or a variety of other consequences. Fortunately, such consequences are often rare, particularly when such surgeries are performed by skilled surgeons. Nevertheless, an increasing number of people are undergoing various types of back surgeries each year. Additionally, there continues to be tremendous increases in medical costs associated with these procedures. As a result, the incidence of unintended or unwanted consequences may rise in a similar fashion. Therefore, providing additional options to physicians for conducting such surgeries is desirable, particularly because such options may aid in reducing such consequences.

SUMMARY

A facet lamina plate system and accompanying methods for utilizing the facet lamina plate system are disclosed. The facet lamina plate system may be utilized during spinal fusion surgeries such as, but not limited to, traditional spinal fusion surgeries, posterior lumbar spinal fusions, supplemental fixations performed after anterior lumbar fusions, or any other suitable type of spinal fusion surgery. Spinal fusion surgeries are utilized to treat a variety of conditions such as, but not limited to, degenerative disc disease, spinal tumors, spinal disc herniations, vertebral fractures, scoliosis, spondylosis, and spondylolisthesis. Spinal fusion surgeries involve fusing or joining together two or more vertebrae of a patient's spine. Often times, supplementary bone grafts, either from the patient or a donor, are utilized in conjunction with the patient's own natural bone growth processes to facilitate a successful fusion. Such spinal fusion surgeries have become increasingly common, and it is estimated that hundreds of thousands of these types of surgical procedures are performed in the world each year.

In particular, the facet lamina plate system may be implanted into a patient's spine during a surgical procedure, such as a spinal fusion procedure or other appropriate procedure. Initially, a surgeon performing the surgical procedure may create an incision in the patient's back and insert a first connection device directly through a first facet joint of the spine of the patient. The first facet joint may be a facet joint that needs to be fused. Once the first connection device is inserted through the first facet joint, the surgeon may insert a second connection device directly through a second facet joint of the spine of the patient. The second facet joint may be contralateral with respect to the first facet joint and may be located at the same level as the first facet joint. As with the first facet joint, the second facet joint may also be associated with the vertebrae that needs to be fused. After the first and second connection devices have been inserted through the first and second facet joints respectively, the surgeon can engage first and second slots of a plate with the first and second connection devices respectively. In one embodiment, the first slot of the plate may be perpendicular to the second slot of the plate, and the first slot may be perpendicular to a long axis of the spine of the patient. However, other arrangements for the slots of the plate are also contemplated in the pending disclosure. Once the plate is engaged with the first and second connection devices in a desired position, the surgeon can tighten or otherwise ensure that the first and second connection devices are firmly affixed to the first and second facet joints respectively. The surgeon may then suture or otherwise close the incision. As a result, the facet lamina plate system stabilizes the spinal segment with the goal of facilitating a successful spinal fusion.

In one embodiment, a facet lamina plate system for securing facet joints of a spine of a patient may be provided. The facet lamina plate system may include a first connection device that may be configured to be positioned directly through a first facet joint of the spine of a patient. Additionally, the system may include a second connection device that may be configured to be positioned directly through a second facet joint of the spine of the patient. The second facet joint may be contralateral with respect to the first facet joint and may be located at the same level as the first facet joint. Furthermore, the system may include a plate that may be configured to engage the first and second connection devices after the first and second connection devices have been positioned through the first and second facet joints respectively. The plate may include a first slot that may be configured to engage the first connection device, and a second slot that may be configured to engage the second connection device. The first slot of the plate may be configured to be perpendicular to the second slot and the first slot may be perpendicular to a long axis of the spine of the patient.

In another embodiment, a method for securing facet joints and vertebrae of a spine of a patient may be provided. The method may include positioning a first connection device directly through a first facet joint of the spine and a second connection device directly through a second facet joint of the spine of the patient. The second facet joint may be contralateral with respect to the first facet joint and may be located at the same level as the first facet joint. Also, the method may include engaging a plate with the first and second connection devices after positioning the first and second connection devices through the first and second facet joints. The plate may include first and second slots such that the first slot may be configured to engage the first connection device and the second slot may be configured to engage the second connection device when engaging the plate. Notably, the first slot may be perpendicular to the second slot and the first slot may be perpendicular to a long axis of the spine of the patient.

In yet another embodiment, another facet lamina plate system for securing facet joints and vertebrae of a spine of a patient may be provided. The facet lamina plate system may include a plate that is positionable in proximity to first and second facet joints of the patient's spine. The first and second facet joints may be right and left facet joints located at the same spinal level of a patient respectively. The plate may include a first interface and a second interface. Additionally, the system may include a first connection device configured to be positioned directly through the first facet joint of the spine of the patient by inserting a shaft portion of the first connection device through a hole in the first interface. The first connection device may be positioned through the first facet joint after the plate is positioned in proximity to the first and second facet joints, wherein a head portion of the first connection device may be configured to rest adjacent to a surface of an indentation in the first interface. The indentation of the first interface may be adjacent to the hole of the first interface. Furthermore, the system may include a second connection device that may be configured to be positioned directly through the second facet joint of the spine of the patient by inserting a shaft portion of the second connection device through a hole in the second interface. The second connection device may be positioned through the second facet joint after the plate is positioned in proximity to the first and second facet joints. A head portion of the second connection device may be configured to rest adjacent to a surface of an indentation in the second interface, which may be located adjacent the hole of the second interface.

In another embodiment, a facet lamina plate kit may be provided. The facet lamina plate kit may include a plurality of connection devices. A first connection device of the plurality of connection devices may be configured to be positioned directly through a first facet joint of a spine of a patient. A second connection device of the plurality of connection devices may be configured to be positioned directly through a second facet joint of the spine of the patient. The second facet joint may be contralateral with respect to the first facet joint and may be located at the same level as the first facet joint. The facet lamina plate kit may further include a plate that may be configured to engage the plurality of connection devices. In one embodiment, the plate may be configured to engage the first and second connection devices after the first and second connection devices have been positioned through the first and second facet joints respectively. The plate of the facet lamina plate kit may include a first slot that may be configured to engage the first connection device. Additionally, the plate may include a second slot that may be configured to engage the second connection device. The first slot may be positioned perpendicular to the second slot, and the first slot may be positioned perpendicular to a long axis of the spine of the patient when the plate is implanted.

In still another embodiment, another facet lamina plate kit may be provided. The facet lamina plate kit may include a plate and a plurality of connection devices. The plate may be configured to be positionable in proximity to a first facet joint and a second facet joint of a spine of a patient. The plate may include a first interface and a second interface. A first connection device of the plurality of connection devices may be configured to be positioned directly through the first facet joint of the spine of the patient by inserting a shaft portion of the first connection device through a hole in the first interface. In one embodiment, the first connection device may be positioned through the first facet joint after the plate is positioned in proximity to the first and second facet joints, wherein a head portion of the first connection device may be configured to rest adjacent to a surface of an indentation in the first interface. The indentation in the first interface may be located adjacent to the hole of the first interface. A second connection device may be configured to be positioned directly through the second facet joint of the spine of the patient by inserting a shaft portion of the second connection device through a hole in the second interface. The second facet joint may be contralateral with respect to the first facet joint and may be located at the same level as the first facet joint. The second connection device may be positioned through the second facet joint after the plate is positioned in proximity to the first and second facet joints. A head portion of the second connection device may be configured to rest adjacent to a surface of an indentation in the second interface. The indentation of the second interface may be adjacent to the hole of the second interface.

These and other features of the facet lamina plate systems, methods, and kits are described in the following detailed description, drawings, and appended claims.

DETAILED DESCRIPTION OF THE INVENTION

Figure 1:
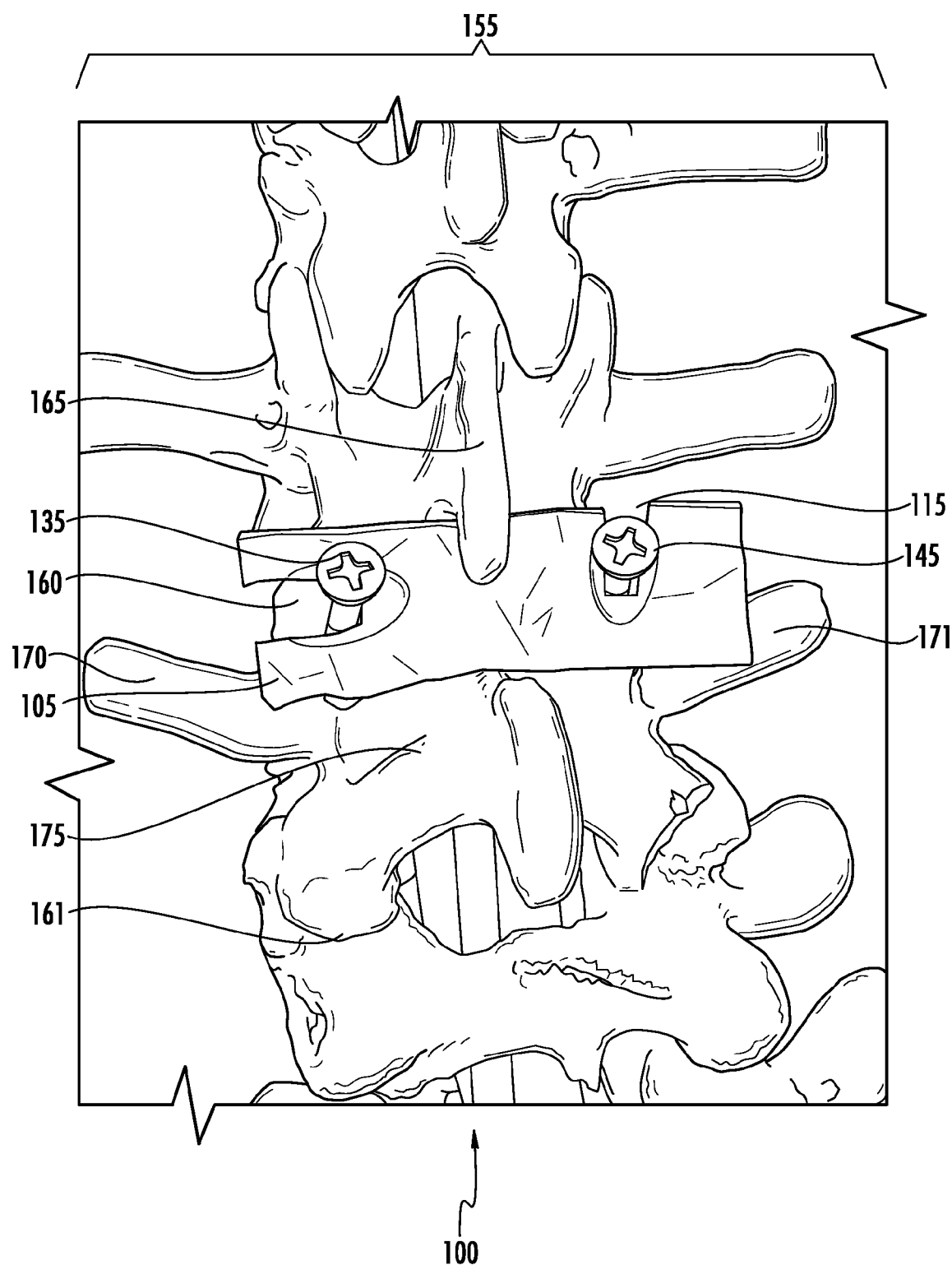
FIG. 1 is an anteroposterior view of a spine of a patient that has a facet lamina plate system implanted onto the spine according to an exemplary embodiment of the present disclosure.

The exemplary embodiments of the present disclosure are described with respect to facet lamina plate systems 100, 700, 1000, 1300, corresponding kits, and methods for securing facet joints of a spine of a patient. Notably, in one embodiment, the facet lamina plate systems 100, 700, 1000, 1300 may be utilized during spinal fusion surgeries such as, but not limited to, traditional spinal fusion surgeries, posterior lumbar spinal fusions, supplemental fixations performed after anterior lumbar fusions, or other types of spinal fusion surgery. In particular, the facet lamina plate systems 100, 700, 1000, 1300 may be implanted onto a patient's spine during a spinal fusion procedure, or other appropriate procedure. In a preferred embodiment, which is illustrated in FIGS. 1-6, a surgeon may create an incision in the patient's back to implant a facet lamina plate system 100, and insert a first connection device 135 of the facet lamina plate system 100 directly through a first facet joint 160 of the spine 155 of the patient. The first facet joint 160 may be a facet joint that is associated with the vertebrae of the spine 155 that need to be fused by the surgeon.

Once the first connection device 135 is inserted through the first facet joint 160, the surgeon may insert a second connection device 145 of the facet lamina plate system 100 directly through a second facet joint 162 of the spine 155 of the patient. The second facet joint may be a contralateral facet joint with respect to the first facet joint, and may be located at the same level as the first facet joint. The second facet joint 162 may also be associated with the vertebrae that need to be fused. The surgeon may then engage first and second slots 110 and 115 of a plate 105 of the facet lamina plate system 100 with the first and second connection devices 135 and 145 respectively. After the plate 105 is engaged with the first and second connection devices 135, 145 in a desired position, the surgeon can then tighten or otherwise affix the first and second connection devices 135, 145 to the first and second facet joints 160, 162 respectively to ensure that the plate 105 and the connection devices 135, 145 are implanted the spine 155. Once the facet lamina plate system 100 is implanted, the surgeon may then suture or otherwise close the incision in the patient's back. As a result, the facet lamina plate system facilitates the mechanism by which the patient's vertebrae can be fused in an effective manner, while also providing long-lasting and/or permanent fixation.

Figure 2:
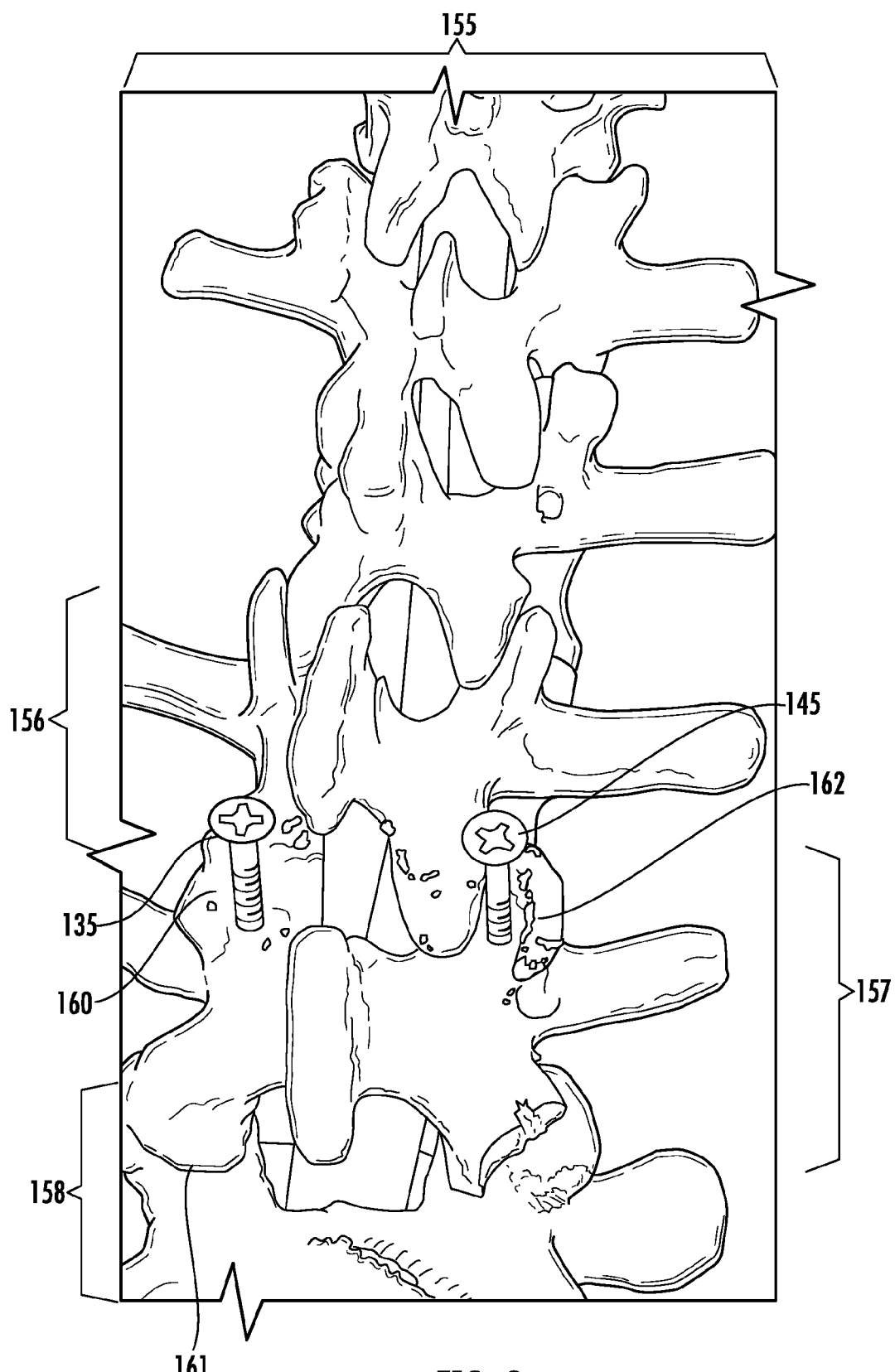
FIG. 2 is an anteroposterior view of a spine of a patient featuring a pair of connection devices inserted directly through facet joints of the spine, wherein the connection devices are a part of the facet lamina plate system of FIG. 1.
Figure 3:
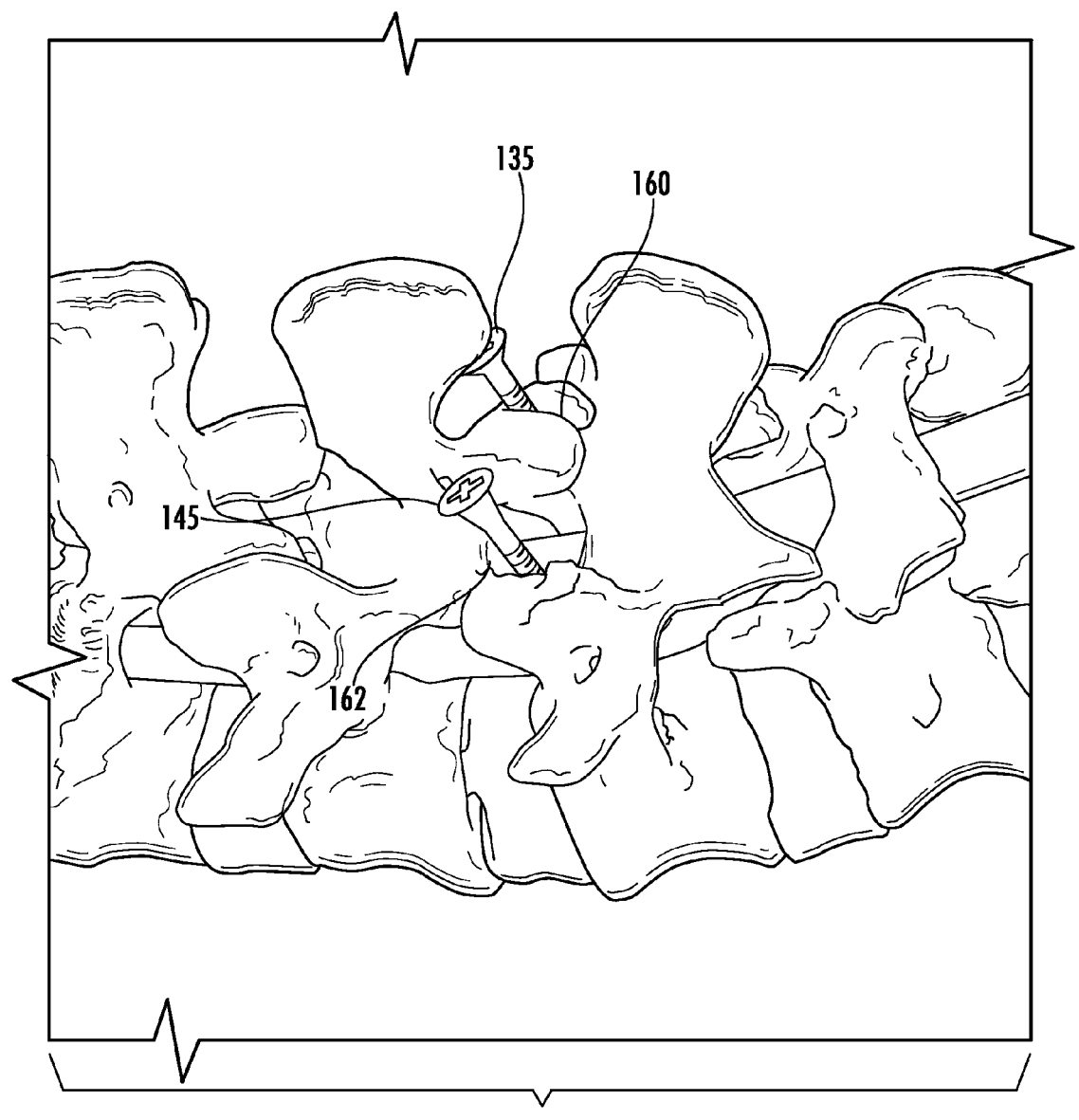
FIG. 3 is a lateral view of a spine of a patient featuring the pair of connection devices of FIG. 2 inserted into facet joints of the spine of the patient.

Referring to the drawings and in particular to FIGS. 1-6 in further detail, the facet lamina plate system 100, according to one embodiment of the invention, is schematically illustrated. The facet lamina plate system 100 may include a plate 105, a first connection device 135, and a second connection device 145. Notably, the facet lamina plate system 100 may be implanted onto the spine 155 of a patient. In FIGS. 1-3, the spine 155 of the patient is illustratively shown as including at least a first vertebra 156, a second vertebra 157, a third vertebra 158, a first facet joint 160 between the first and second vertebrae 156 and 157, a second facet joint 162 between the first vertebra 156 and second vertebra 157, a third facet joint 161 between the second vertebra 157 and the third vertebra 158, a spinous process 165, a first transverse process 170, a second transverse process 171, and lamina 175. Of course, the spine 155 may include any of the other traditional structural features of a spine such as, but not limited to, vertebral bodies, pedicles, a spinal canal, and other such structural features.

Referring more specifically to FIGS. 1 and 4-6, the plate 105 of the facet lamina plate system 100 may be utilized to provide a supporting mechanism to help achieve an effective fusion. In one embodiment, the plate 105 may be rectangular in shape. However, the plate 105 may also conform to the shape of the spine 155, conform to the shape of the lamina 175, conform to the shape of the facet joints 160, 161, 162, have a square shape, have a "U" shape, or have any other desired shape that may assist in achieving fusion of vertebrae. In one embodiment, the plate 105 may be made of titanium, however, any suitable material may be utilized such as, but not limited to, steel, suitable non-metallic compounds, plastics, or any other suitable material. In one embodiment, the plate 105 may include a first slot 110 having a pair of indentations 120, 121 adjacent to either side of the first slot 110. Additionally, the plate 105 may include a second slot 115 having a pair of indentations 125, 126 adjacent to either side of the second slot 115. The plate 105 may further include a notch 130 that may be configured to engage a bottom portion (or any other desired portion) of the spinous process 165 of the spine 155 once the plate 105 is implanted onto the spine 155 of the patient. In one embodiment, the first slot 110 may be positioned perpendicular to the second slot 115, and the first slot may be configured to be perpendicular to a long axis of the spine 155 when the plate 105 is implanted onto the spine 155 of the patient. In certain other embodiments, the first slot 110 and the second slot 115 may be positioned at any desired angle with respect to each other or with respect to the spine 155.

Figure 4:
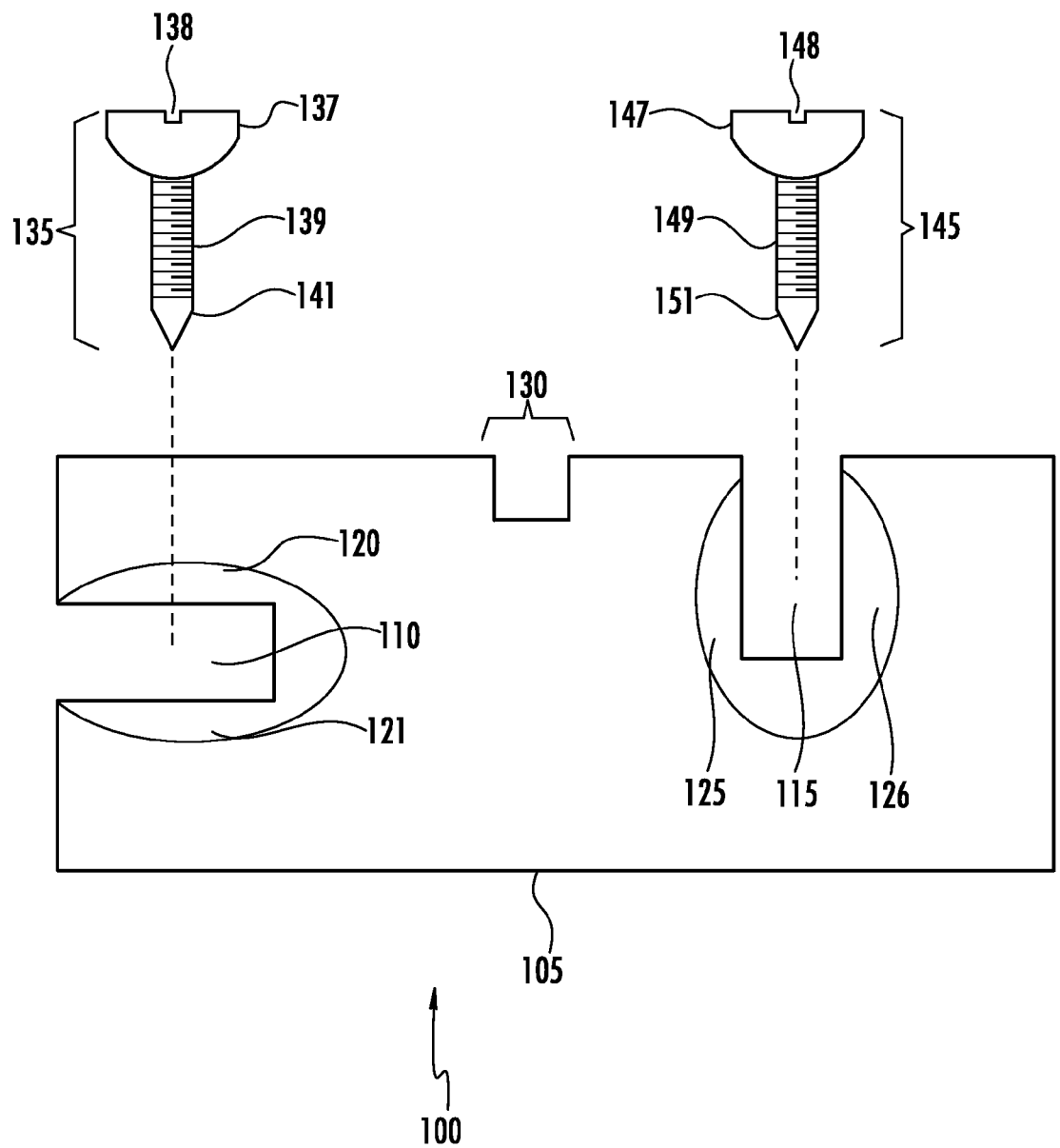
FIG. 4 is an exploded top view of the facet lamina plate system of FIG. 1 featuring a pair of connection devices and a plate according to an embodiment of the present disclosure.
Figure 5:
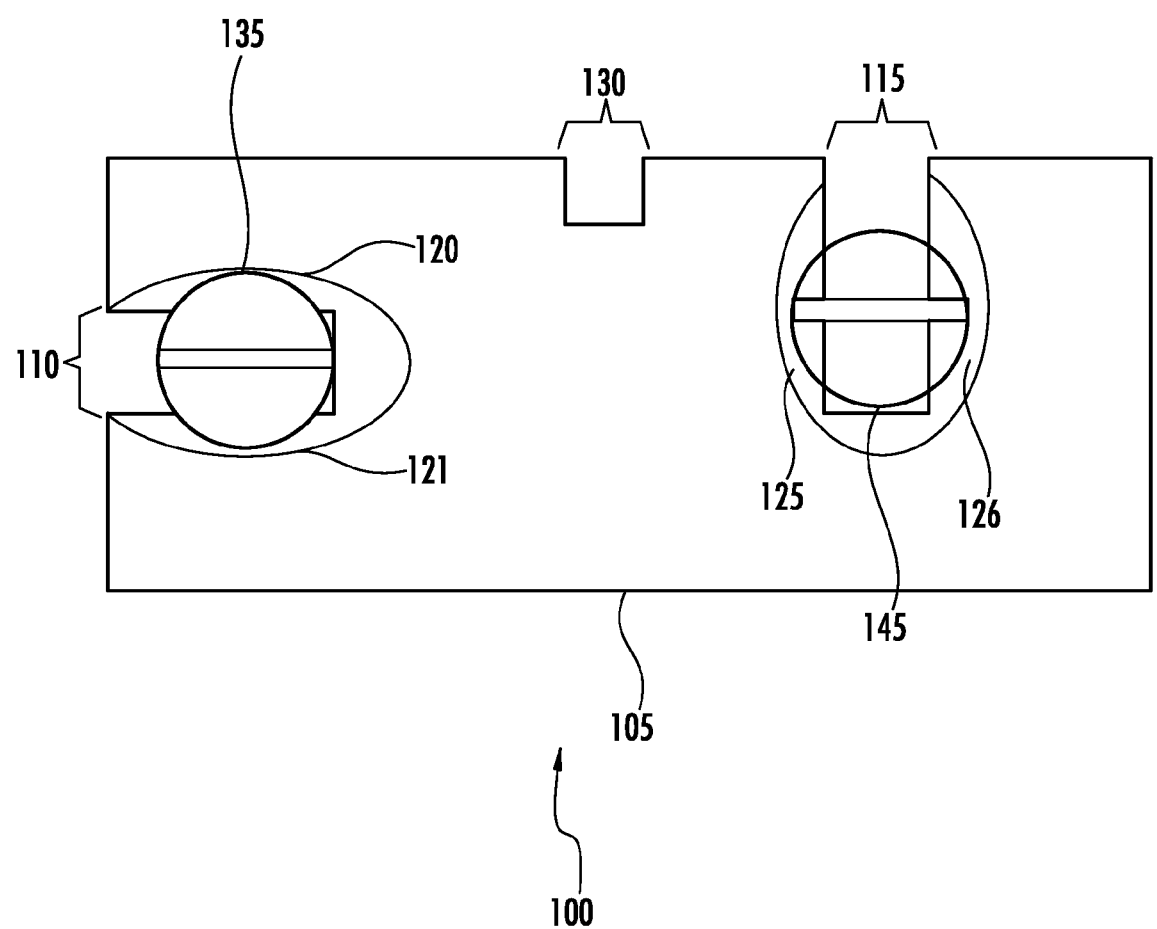
FIG. 5 is a top view of the facet lamina plate system of FIG. 1 featuring two connection devices engaged with slots of a plate of the system.
Figure 6:
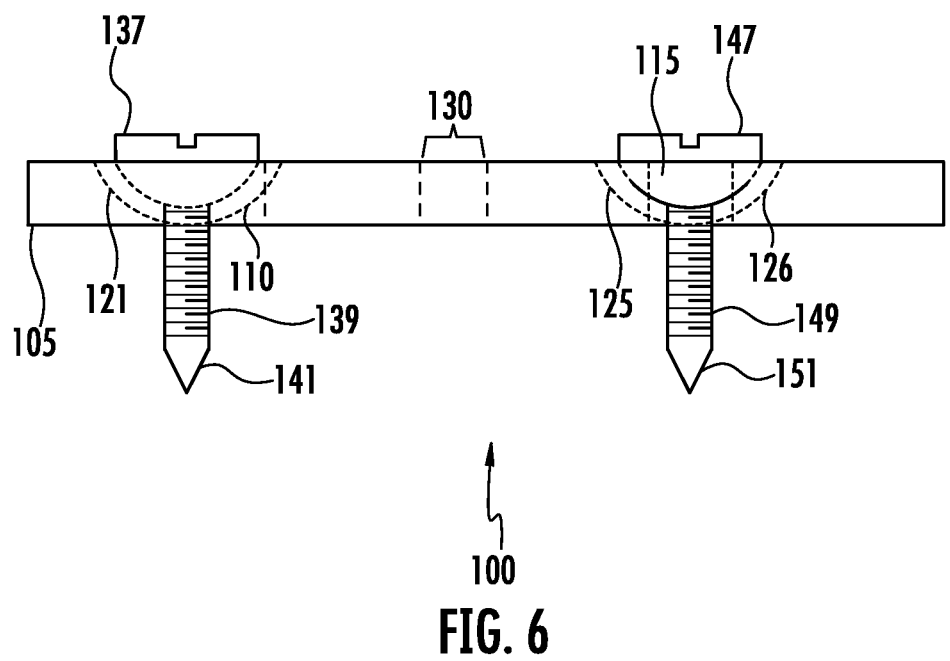
FIG. 6 is a side view of the facet lamina plate system of FIG. 1 featuring two connection devices engaged with slots of a plate of the system.

With regard to the first slot 110 of the plate 105, indentation 120 may be positioned on one side adjacent to the first slot 110 and indentation 121 may be positioned on the other side adjacent to the first slot 110. Illustratively, the positioning of the indentations 120, 121 with respect to the first slot 110 may be seen in FIGS. 4-5. With regard to the second slot 115, indentation 125 may be positioned on one side adjacent to the second slot 115 and indentation 126 may be positioned on the other side adjacent to the second slot 115. Illustratively, the positioning of the indentations 125, 126 may be seen in FIGS. 4-5. In one embodiment, each of the indentations 120, 121, 125, 126 may be half-hemispherical interfaces as illustrated in FIGS. 4-6. In another embodiment, the indentations 120, 121, 125, 126 may be interfaces such that when first and second connection devices 135 and 145 are inserted into the slots 110 and 115 respectively, a portion of the head 137 of the first connection device 135 can rest on the indentations 120 and 121, and a portion of the head 147 of the second connection device 145 can rest on the indentations 125 and 126. The resting of the portion of the head 137 in the indentations 120 and 121, and the resting of the portion of the head 147 in the indentations 125 and 126 are schematically shown in FIGS. 5-6. When the heads 137 and 147 rest on the indentations 120, 121, 125, and 126, it may create, in essence, a ball-cup interface, which can allow the seating of the connection devices 135 and 145 on the plate 105 to occur at varying desired angles and can allow the plate 105 to move with respect to the connection devices 135 and 145 at various degrees of freedom. In certain embodiments, the plate 105 may include any number of slots 110 and 115, and a portion of the heads 137 and 147 of the first and second connection devices 135 and 145 may be wider than the widths of the first and second slots 110 and 115.

Figure 7:
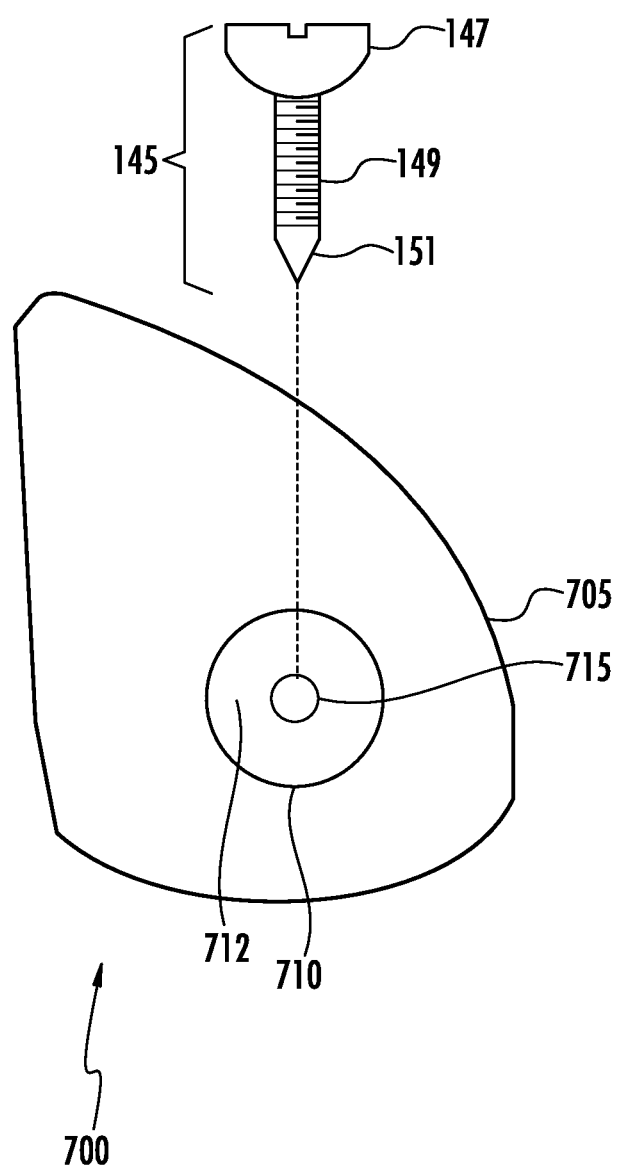
FIG. 7 is an exploded top view of a facet lamina plate system according to another embodiment of the present disclosure.

With regard to the first connection device 135 of the facet lamina plate system 100, the first connection device 135 may include a head 137, a shaft portion 139, and a tip 141. Similarly, the second connection device 145 of the facet lamina plate system 100 may include a head 147, a shaft portion 149, and a tip 151. In certain embodiments, the first connection device 135 and the second connection device 145 may be screws, tapping screws, self-drilling screws, fasteners, nails or any other type of connection device. In certain embodiments, the first and second connection devices 135 and 145 may be made of titanium, stainless steel, plastics, or any other suitable material. The head portions 137 and 147 may have slots 138 and 148 respectively, which may be configured to receive an end of a screwdriver or other similar device so that the first and second connection devices may be screwed into the facet joints 160, 162 or into other desired areas of the spine 155 by using the screwdriver. In one embodiment, instead of having slots 138 and 148 as shown in FIGS. 5-7, the head portions 137 and 147 may have star-shaped slots configured to receive a star-shaped end of a screwdriver or other similar device. In certain other embodiments, the head portions 137 and 147 may have any type of notch or slot contained therein. In addition to the head portions 137 and 147, the first connection device 135 may include a shaft portion 139, and the second connection device 145 may include may include a shaft portion 149. In one embodiment, the shaft portions 139 and 149 may have threading similar to a traditional screw so that the first and section connection devices 135 and 145 may be screwed in readily into the facet joints 160 and 162 or other desired locations of the spine 155. Also, the first connection device 135 may include a tip 141, and the second connection device may include a tip 151. The tips 141 and 151 may be pointed much like the end of a traditional screw such that the first and second connection devices 135 and 145 can experience minimal resistance when being positioned through the facet joints 160 and 162 or other desired locations. In certain embodiments, a greater or lesser number of connection devices 135 and 145 may be utilized.

During an operation, a surgeon may implant the facet lamina plate system 100 onto a spine 155 of a patient in the following manner. Initially, the surgeon may create an incision in the patient's back to expose the spine 155 of the patient for a spinal fusion surgical procedure. Once the spine 155 is exposed, the surgeon can locate the vertebrae, such as vertebrae 156 and 157, or other spinal structures that need to be fused during the procedure. After the surgeon has located the first facet joint 160 and the second facet joint 162, the surgeon may utilize a drill or other tool to drill directly through each of the facet joints 160 and 162 to create holes for the first connection device 135 and the second connection device 145 to be inserted into by the physician. At this point, the physician may position the first connection device 135 into the hole drilled in the first facet joint 160 and the second connection device 145 into the hole drilled in the second facet joint 162 either by hand or by utilizing a tool, such as a screwdriver or other similar tool. In one embodiment, the first and second connection devices 135 and 145 may be inserted into the pedicles of the vertebrae 156 and 157 as well. In one embodiment, instead of using a drill or other similar device to drill holes into the facet joints 160 and 162, the surgeon may utilize the first and second connection devices 135 and 145 themselves to create the holes through the first and second facet joints 160 and 162. For example, if the first and second connection devices 135 and 145 are self-drilling or tapping screws, the surgeon can simply tap on the head 137 of the first connection device 135 to insert the first connection device 135 directly through the first facet joint 160. Similarly, the surgeon can tap on the head 147 of the second connection device 145 to insert the second connection device 146 directly through the second facet joint 162.

Once the first and second connection devices 135 and 145 are positioned in the first and second facet joints 160 and 162 respectively, the surgeon can then engage the first slot 110 of the plate 105 with the first connection device 135 and engage the second slot 115 of the plate 105 with the second connection device 145. As noted herein, the first slot 110 may be perpendicular to the second slot 115, and the first slot may be perpendicular to a long axis of the spine 155 when the plate 105 is engaged with the first and second connection devices 135 and 145. By having the first slot 110 and the second slot 115 of the plate 105 being perpendicular with respect to each other, this may maximize the ability to initially place the first and second connection devices 135 and 145 in an optimal position prior to engaging the plate 105 with the first and second connection devices 135 and 145. Additionally, if the slots 110 and 115 are perpendicular with respect to each other, this may also ensure that once the plate 105 is engaged with the first and second connection devices 135 and 145, the plate 105 is effectively secured in an optimally desired position, while also ensuring that the plate 105 does not move unnecessarily once secured. In one embodiment, once the plate 105 is engaged with the first slot 110 and the second slot 115, the notch 130 of the plate 105 may be configured to engage the spinous process 165. By engaging the notch 130 with the spinous process 165, this may provide an additional means of securing the plate 105 to the vertebrae 156 and 157 and to the first and second connection devices 135 and 145.

In one embodiment, once the plate 105 is engaged with the first and second connection devices 135 and 145, the surgeon can further secure the first and second connection devices 135 and 145 of the facet lamina plate system 100 by, for example, utilizing a screwdriver or other device to fully tighten the first and second connection devices 135 and 145 onto the facet joints 160 and 162. This may allow the facet lamina plate system 105 to be securely implanted onto the spine 155 of the patient. At this point, the surgeon may close the incision over the facet lamina plate system 100 so that the patient can begin the healing process. In one embodiment, the facet lamina plate system 100 can be permanently implanted onto the patient's spine 155. However, in other embodiments, the facet lamina plate system 100 can be removed if a revision surgery is necessary, or if the surgeon determines that vertebrae 156 and 157 have been effectively fused after a period of time and that the patient no longer needs the facet lamina plate system 100 implanted onto the spine 155.

Figure 8:
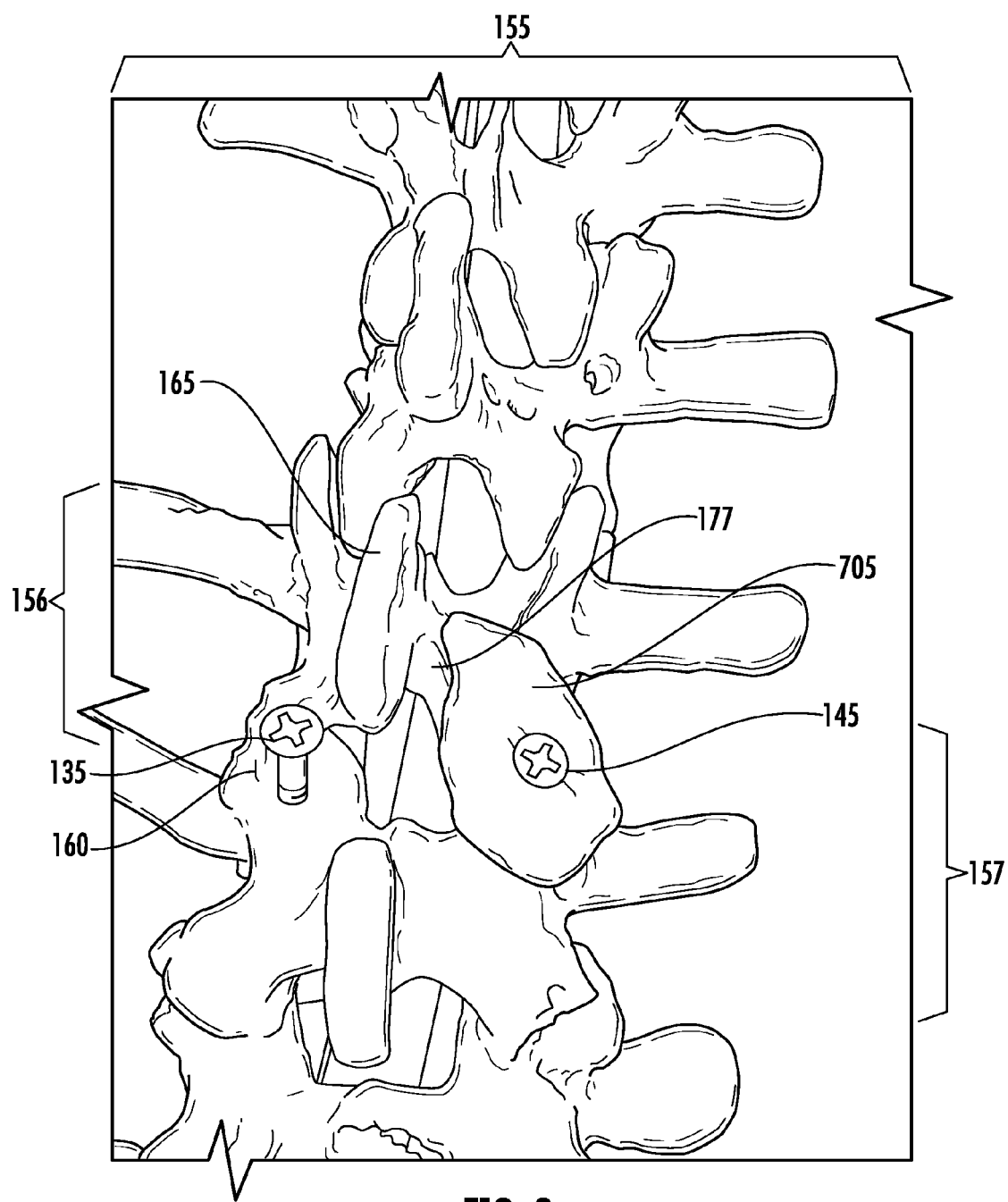
FIG. 8 is an anteroposterior view of a spine implanted with the facet lamina plate system of FIG. 7.
Figure 9:
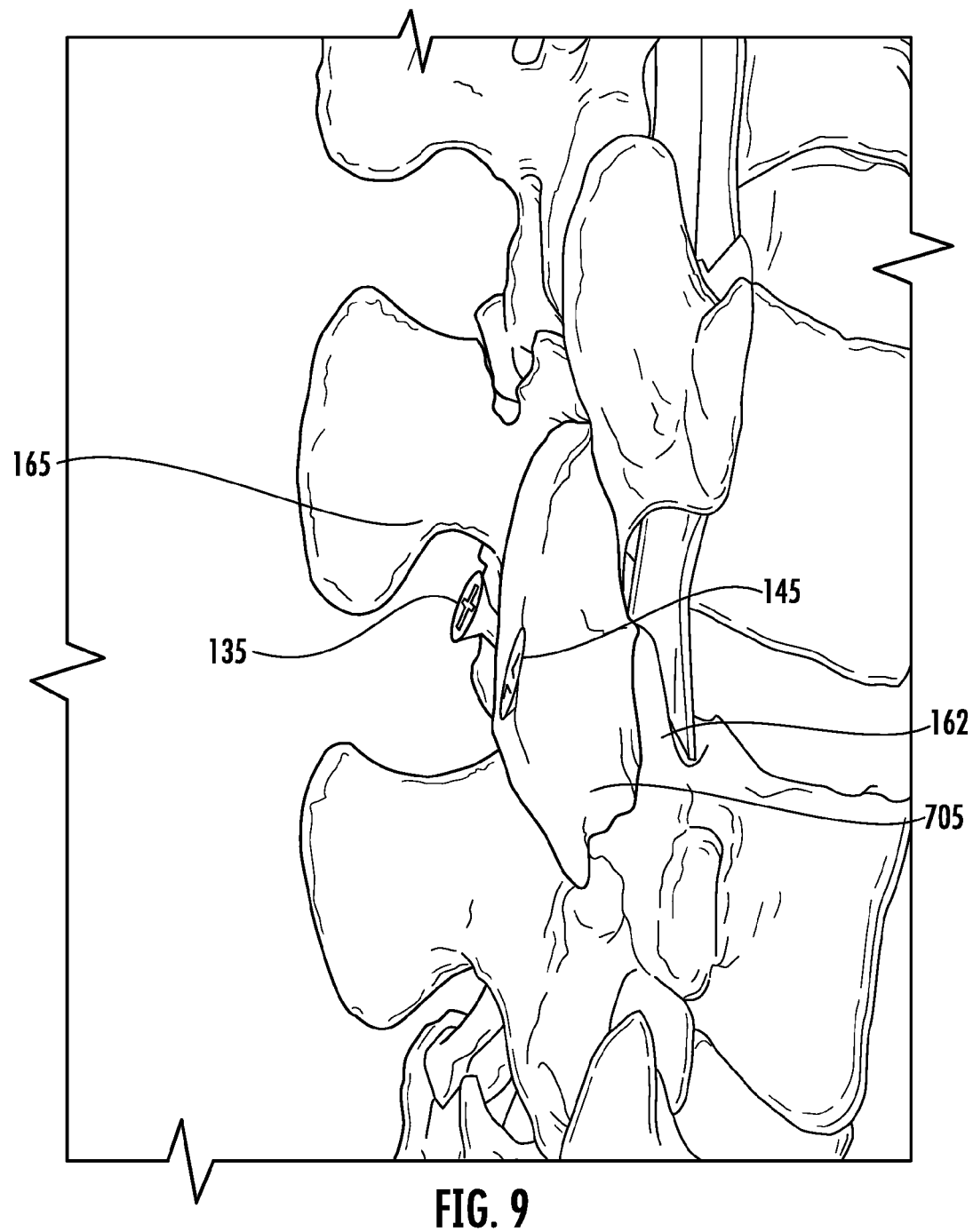
FIG. 9 is a lateral view of a spine implanted with the facet lamina plate system of FIG. 7.

Referring to the drawings and in particular to FIGS. 7-9, another facet lamina plate system 700 is schematically illustrated. In this embodiment, instead of inserting the first and second connection devices 135, 145 in the facet joints 160, 162 before engaging a plate or implant, the first and second connection devices 135, 145 may be inserted into the facet joints 160, 162 after a plate or implant is positioned over the facet joints 160, 162 first. The facet lamina plate system 700 may include the first and second connection devices 135 and 145, one or more implants 705, an interface 710, an indentation 712 within the interface 710, and a hole 715. Each implant 705 may be utilized to cover the facet joints, such as facet joints 160 and 162, and may be configured to extend up over the lamina 177. By allowing each implant 705 to cover a particular facet joint 160 or 162, or both, the first and second connection devices 135 and 145 may be directly inserted through the facet joints 160 and 162. The interface 710 of the implant 705 may be an area of the implant 705 that may be configured to receive either the first or second connection device 135, 145 to secure the implant 705 to a particular facet joint 160, 162. In one embodiment, the interface 710 may include the indentation 712, which may be configured to allow a portion of a head 137, 147 of the first or second connection devices 135, 145 to rest adjacent to a surface of the indentation 712 when the first or second connection device 135, 145 is inserted through hole 715 of the interface 710. In one embodiment, the indentation 712 may be hemispherical in shape or any other shape that may conform to the shape of the heads 137, 147 of the first and second connection devices 135 and 145.

During a surgical procedure, a surgeon may implant the facet lamina plate system 700 onto a spine 155 of a patient in the following manner. To begin the surgical procedure, the surgeon may create an incision in the patient's back to expose the spine 155 of the patient for the surgical procedure. Once the spine 155 is exposed, the surgeon can locate the vertebrae, such as vertebrae 156 and 157, that need to be fused. After the surgeon has located the first facet joint 160 and the second facet joint 162, the surgeon may utilize a drill or other tool to drill directly through each of the facet joints 160 and 162 to create holes for the first connection device 135 and the second connection device 145 to be inserted into by the physician. At this point, the physician may position the implant 705 over a particular facet joint, such as facet joint 162 in this example, into a desired position. The surgeon may then insert, as shown in FIGS. 8 and 9, the second connection device 145 through the hole 715 in the interface 710 to secure the implant 705 onto the facet joint 162. The surgeon may repeat the process for facet joint 160 if another implant 705 is needed for facet joint 160. Once the implant 705 is secured, the surgeon can close the incision to allow the patient to heal.

Figure 10:
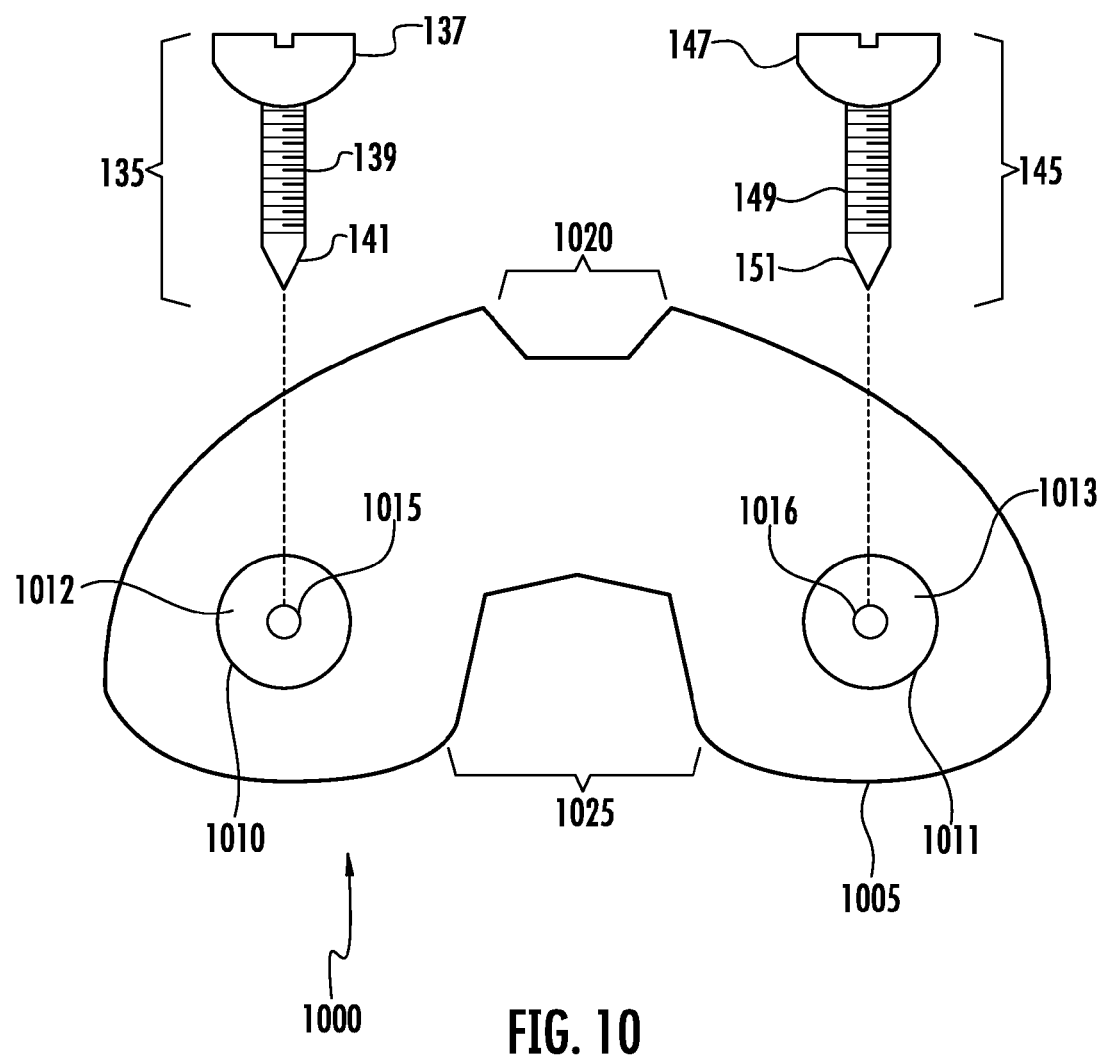
FIG. 10 is an exploded top view of a facet lamina plate system according to yet another embodiment of the present disclosure.
Figure 11:
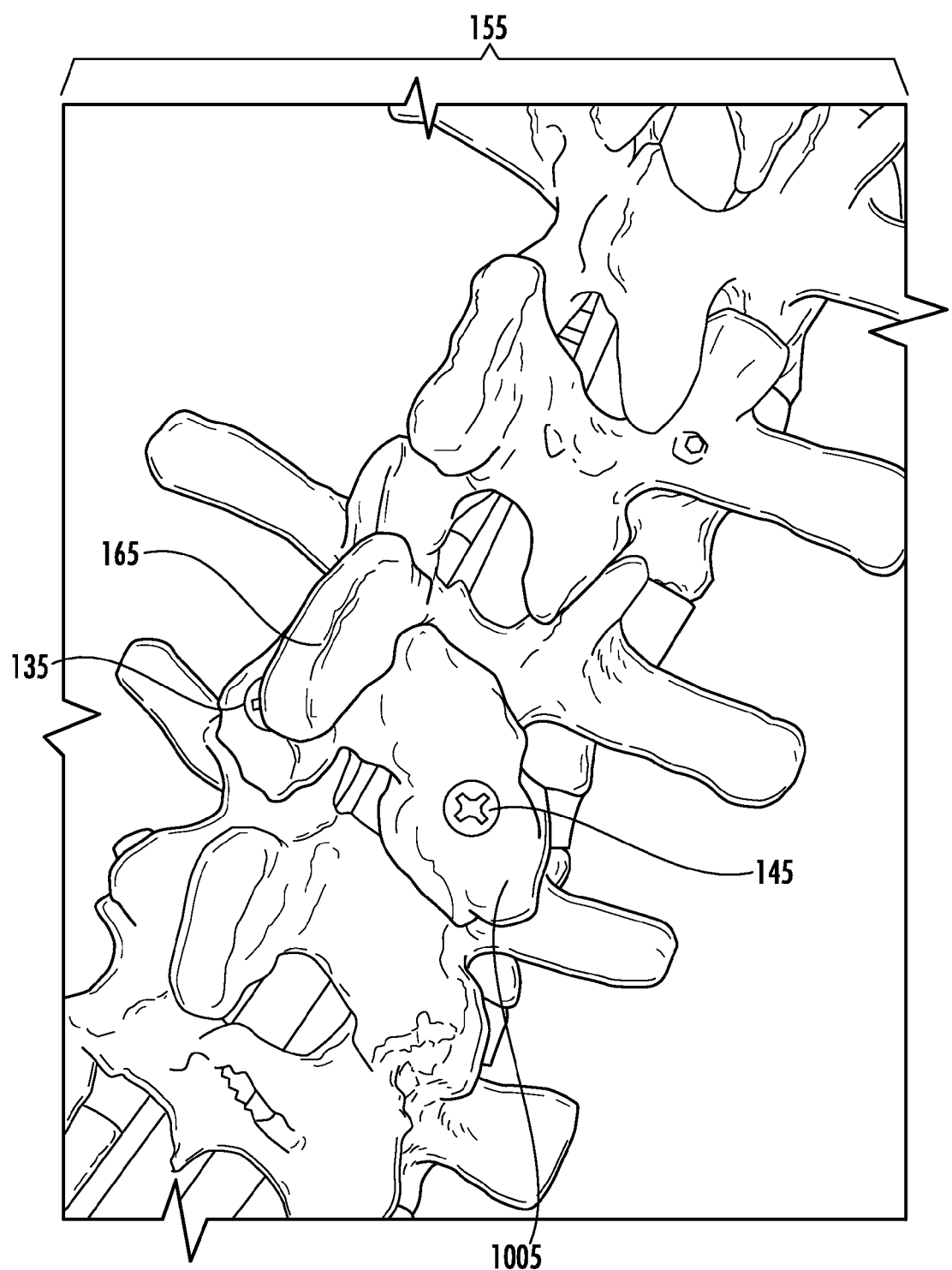
FIG. 11 is an angled anteroposterior view of a spine implanted with the facet lamina plate system of FIG. 10.
Figure 12:
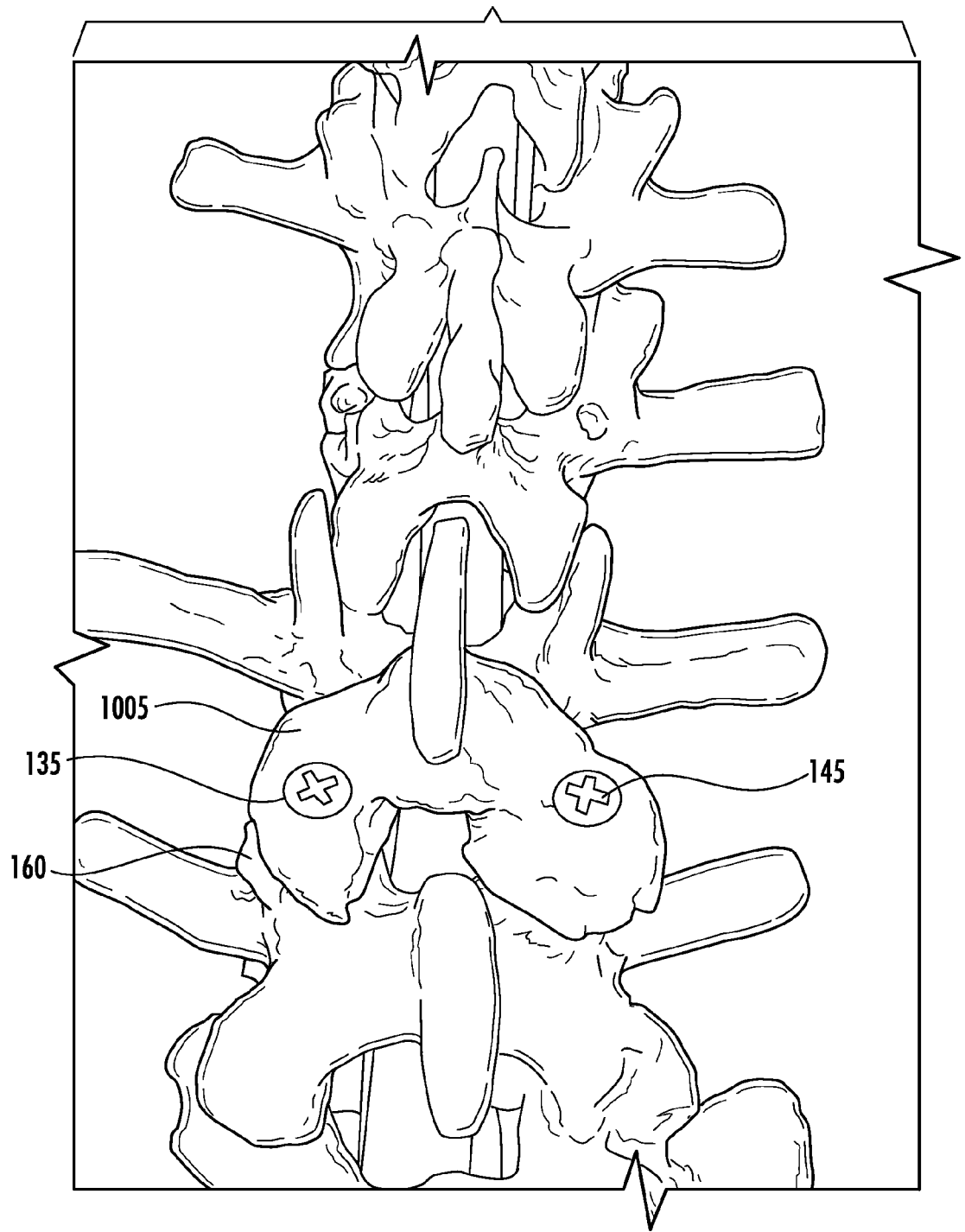
FIG. 12 is an anteroposterior view of a spine implanted with the facet lamina plate system of FIG. 10.

Referring to the drawings and in particular to FIGS. 10-12, yet another facet lamina plate system 1000 is schematically illustrated. The facet lamina plate system 1000 may include the first and second connection devices 135 and 145, a plate 1005, a left interface 1010, a right interface 1011, a left indentation 1012, a right indentation 1013, a left hole 1015, a right hole 1016, a notch 1020, and a notch 1025. The plate 1005 may be utilized to cover the facet joints, such as facet joints 160 and 162, and can engage the spinous process 165. When the plate 1005 is positioned in a desired position over the facet joints 160 and 162, the first and second connection devices 135 and 145 may be directly inserted through the facet joints 160 and 162 after the plate 1005 is positioned. The interfaces 1010 and 1011 may be areas of the plate 1005 that may be configured to receive the first and second connection devices 135 and 145 to secure the plate 1005 to the facet joints 160 and 162. In one embodiment, the left interface 1010 may include an indentation 1012, which may be configured to allow a portion of a head 137, 147 of the first or second connection devices 135, 145 to rest adjacent to a surface of the indentation 1012 when the first or second connection device 135, 145 is inserted through hole 1015 of the interface 1010. Similarly, the right interface 1011 may include an indentation 1013, which may be configured to allow a portion of a head 137, 147 of the first or second connection devices 135, 145 to rest adjacent to a surface of the indentation 1013 when the first or second connection devices 135, 145 is inserted through the hole 1016 of the interface 1011. In one embodiment, the indentations 1012 and 1013 may be partially hemispherical in shape or any other shape that may conform to the shape of the heads 137, 147 of the first and second connection devices 135 and 145.

The facet lamina plate system 1000 may be implanted onto a spine 155 of a patient in the following exemplary manner. The surgeon may create an incision in the patient's back to expose the spine 155 of the patient for a surgical procedure. Once the spine 155 is exposed, the surgeon can locate the vertebrae, such as vertebrae 156 and 157, that need to be fused during the procedure. Once the surgeon has located the facet joints 160, 162, the surgeon may utilize a drill or other tool to drill directly through each of the facet joints 160 and 162 to create holes for the first connection device 135 and the second connection device 145 to be inserted into. The surgeon may then position the plate 1005 over the facet joints 160 and 162 into a desired position. The notch 1020 of the plate 1005 may engage a bottom portion of the spinous process 165 so as to ensure a secure fit. The notch 1025 may exist, in part, to minimize the amount of material in the plate 1005 that is used for the facet lamina plate system 1000 and to prevent the plate 1005 from unnecessarily touching other areas of the spine 155. The surgeon may then insert, as shown in FIGS. 11 and 12, the first and second connection devices 135 and 145 through the holes 1015 and 1016 of the plate 1005 respectively to secure the plate 1005 onto the facet joints 160 and 162. Once the facet lamina plate system 1000 is secured, the surgeon can close the incision and complete the surgical procedure.

Figure 13:
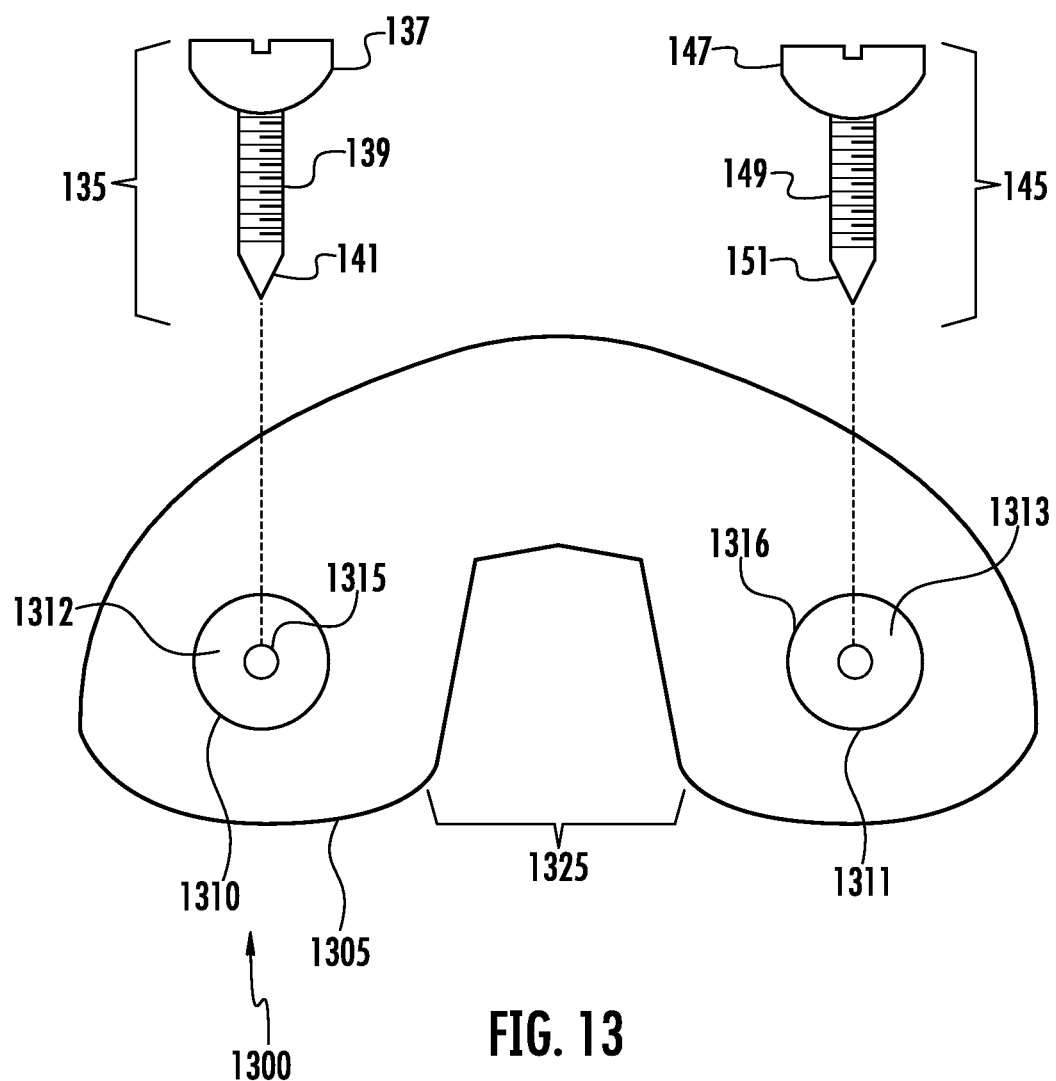
FIG. 13 is an exploded top view of a facet lamina plate system according to still another embodiment of the present disclosure.
Figure 14:
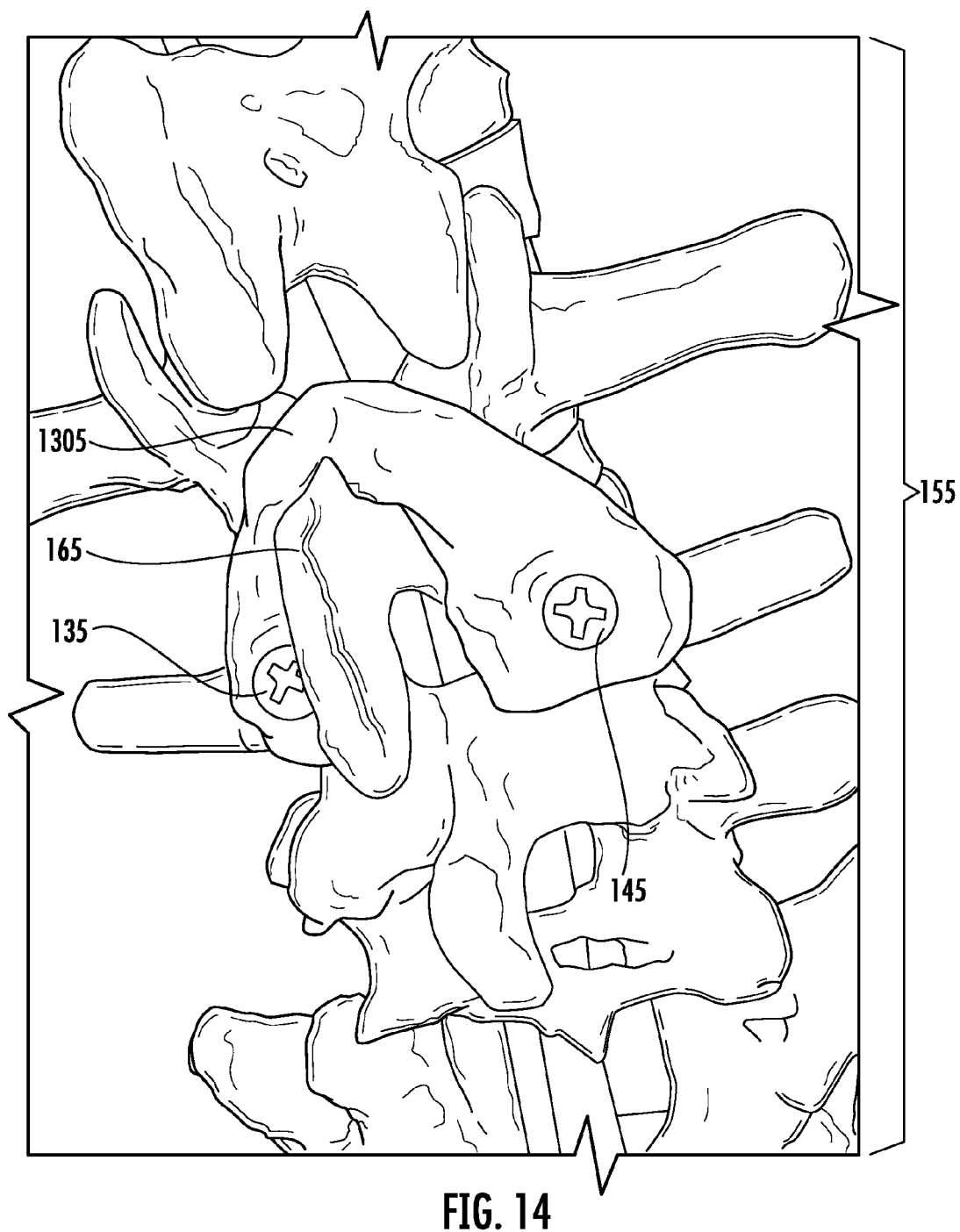
FIG. 14 is an angled anteroposterior view of a spine implanted with the facet lamina plate system of FIG. 13.
Figure 15:
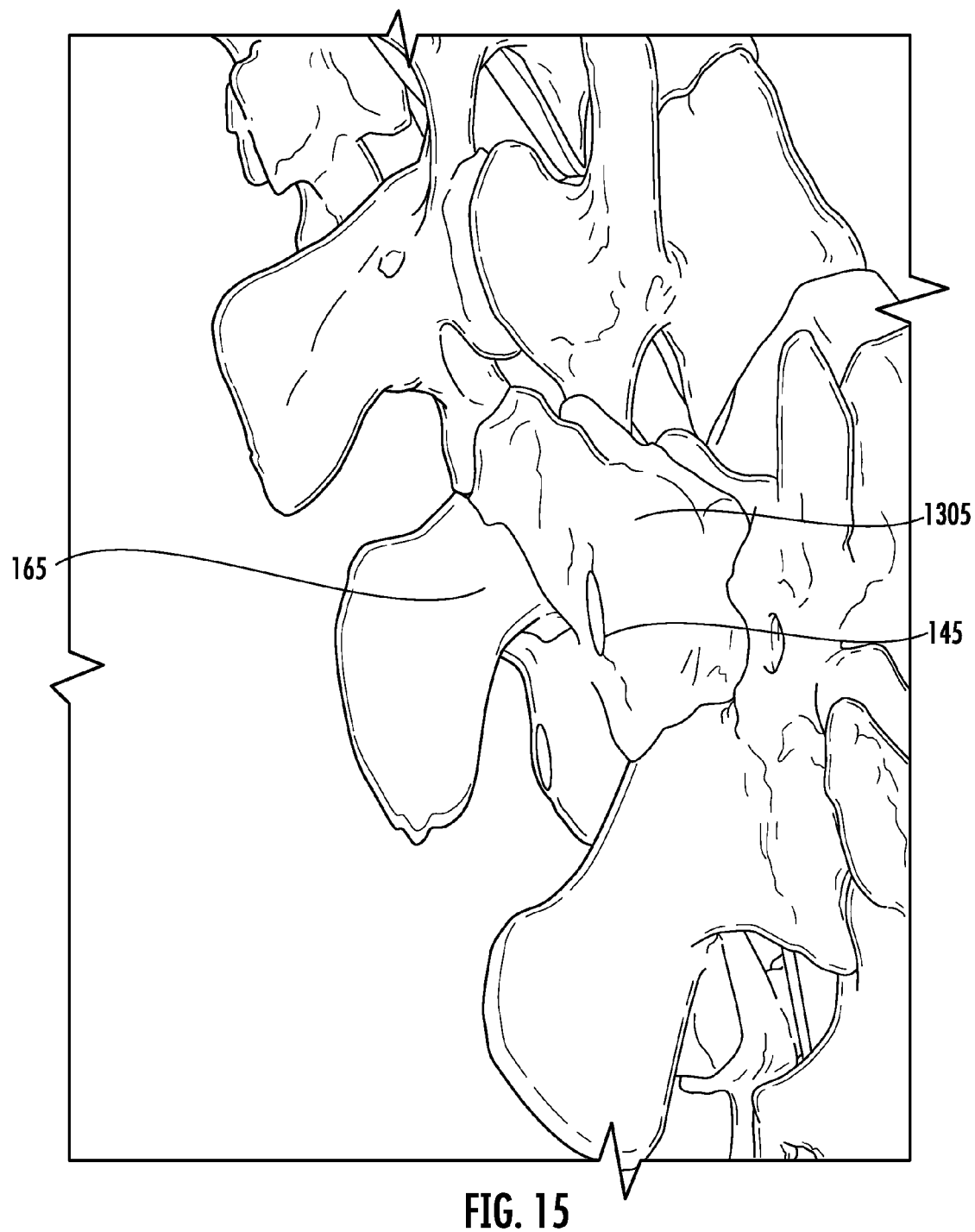
FIG. 15 is a lateral view of a spine of a patient implanted with the facet lamina plate system of FIG. 13.

Referring to the drawings and in particular to FIGS. 13-15, still another facet lamina plate system 1300 is schematically illustrated. The facet lamina plate system 1300 may include the first and second connection devices 135 and 145, a plate 1305, a left interface 1310, a right interface 1311, a left indentation 1312, a right indentation 1313, a left hole 1315, a right hole 1316, and a notch 1325. The plate 1305 may be utilized to cover the facet joints, such as facet joints 160 and 162, extend up over the lamina 177, and can engage the top of the spinous process 165. When the plate 1305 is positioned in a desired position over the facet joints 160 and 162 and the spinous process 165, the first and second connection devices 135 and 145 may be directly inserted through the facet joints 160 and 162 shortly afterwards. The interfaces 1310 and 1311 may be areas of the plate 1305 that may be configured to receive the first and second connection devices 135 and 145 to secure the plate 1305 to the facet joints 160 and 162. In one embodiment, the left interface 1310 may include an indentation 1312, which may be configured to allow a portion of a head 137, 147 of the first or second connection devices 135, 145 to rest adjacent to a surface of the indentation 1312 when the first or second connection device 135, 145 is inserted through hole 1315 of the interface 1310. Similarly, the right interface 1311 may include an indentation 1313, which may be configured to allow a portion of a head 137, 147 of the first or second connection devices 135, 145 to rest adjacent to a surface of the indentation 1313 when the first or second connection devices 135, 145 is inserted through the hole 1316 of the interface 1311. In one embodiment, the indentations 1312 and 1313 may be partially hemispherical in shape or may be any other shape that may conform to the shape of the heads 137, 147 of the first and second connection devices 135 and 145.

In one embodiment, the facet lamina plate system 1300 may be implanted onto a spine 155 of a patient in the following exemplary manner. The surgeon may begin the surgical procedure by creating an incision in the patient's back to expose the spine 155 of the patient for the procedure.

Once the spine 155 is exposed, the surgeon can locate the vertebrae, such as vertebrae 156 and 157, that need to be fused during the procedure. Once the surgeon has located the facet joints 160, 162, the surgeon may utilize a drill or other tool to drill directly through each of the facet joints 160 and 162 to create holes for the first connection device 135 and the second connection device 145 to be inserted into. The surgeon may then position the plate 1305 over the facet joints 160 and 162 and over a top portion of the spinous process 165 into the desired position. The notch 1325 of the plate 1005 may engage the top portion of the spinous process 165 so as to ensure a secure fit. The surgeon may then insert, as shown in FIGS. 14 and 15, the first and second connection devices 135 and 145 through the holes 1315 and 1316 respectively to secure the plate 1305 onto the facet joints 160 and 162. Once the facet lamina plate system 1300 is secured, the surgeon can close the incision and complete the surgical procedure.

Notably, the facet lamina plate systems 100, 700, 1000, 1300 may also be provided as a kit to various surgeons, hospitals, or other users. The kit may separately include the plate 105, plate 705, plate 1005, plate 1305, the first connection device 135, and the second connection device 145, or various combinations of any of these components. In an embodiment, the kit may be configured to include additional plates of varying shapes and sizes, along with connection devices that correspond to the additional plates of varying shapes and sizes. In another embodiment, each of the items that are part of the facet lamina plate systems 100, 700, 1000, 1300 may be packaged separately. The kit may also include instructions for assembling and disassembling the facet lamina plate systems 100, 700, 1000, 1300. Additionally, the kit may include instructions for performing spinal fusion surgeries using the facet lamina plate systems 100, 700, 1000, 1300 as well. Furthermore, the instructions may include various steps for using the facet lamina plate systems 100, 700, 1000, 1300 based on the type of procedure to be performed on a particular patient.

Figure 16:
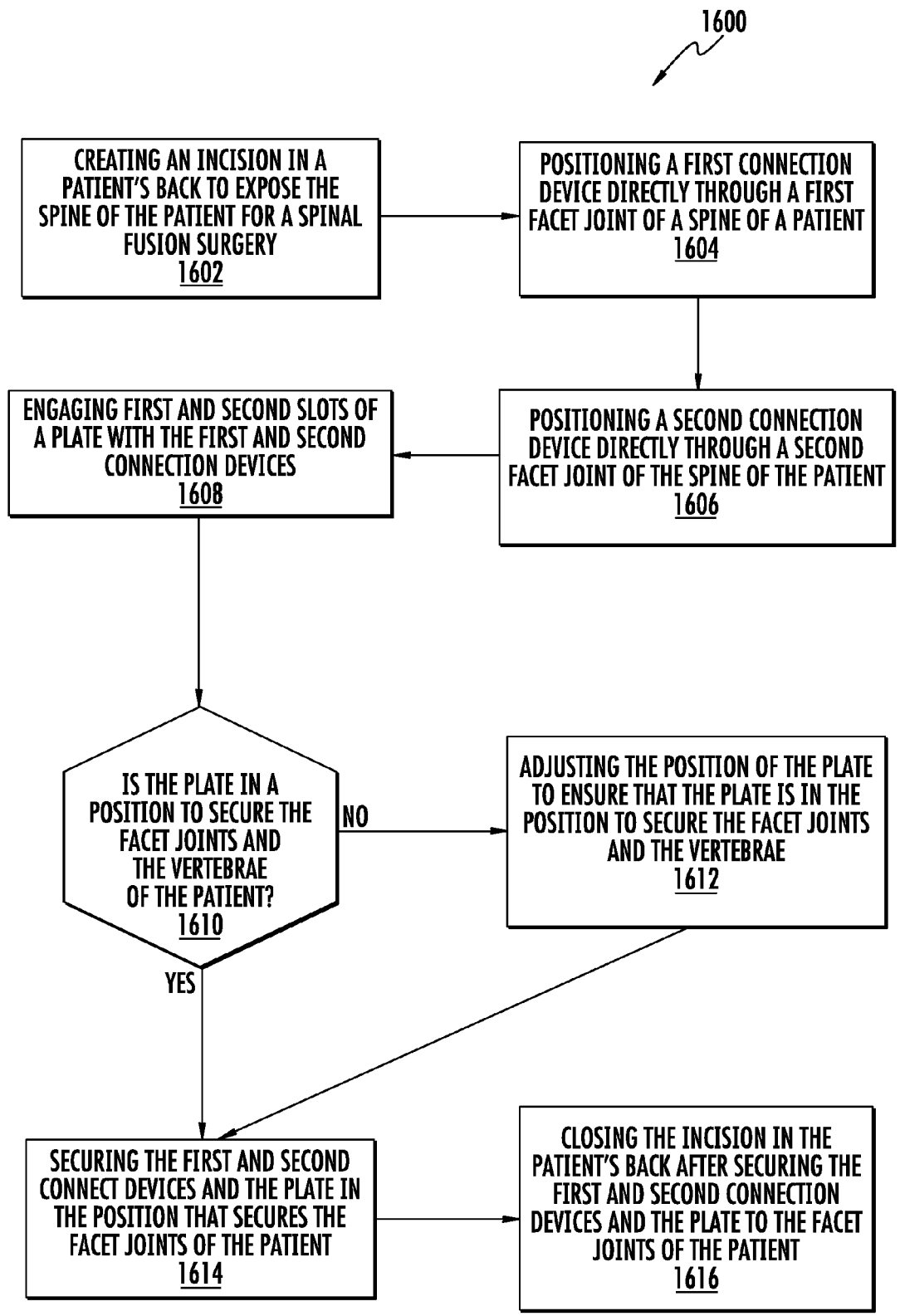
FIG. 16 features a method for securing facet joints of a spine of a patient according to an exemplary embodiment of the present disclosure.

Referring now also to FIG. 16, an exemplary method 1600 for securing facet joints of a spine of a patient is schematically illustrated. The method 1600 may include, at step 1602, creating an incision in a patient's back to expose the spine 155 of the patient in preparation of a spinal fusion surgery or other suitable surgery. In one embodiment, the incision may be created at a location where vertebrae of the spine 155 need to be fused. At step 1604, the method 1600 may include positioning a first connection device 135 directly through a first facet joint 160 of the spine 155 of the patient. The method 1600 may then include, at step 1606, positioning a second connection device 145 directly through a second facet joint 162 of the spine 155 of the patient. Once the first and second connection devices 135, 145 are positioned through the first and second facet joints 160, 162 respectively, the method 1600 may include engaging the plate 105 with the first and second connection devices 135, 145, at step 1608. In one embodiment, the plate may be plate 705, plate 1005, plate 1305, or any other suitable plate. In one embodiment, when the plate 105 is engaged with the first and second connection devices 135, 145, the first slot 110 and the second slot 115 of the plate 105 may be engaged with the first and second connection devices 135, 145 respectively.

At step 1610, the method 1600 may include determining if the plate 105 is in a position to secure the first and second facet joints 160, 162 and the vertebrae 156, 157 of the patient such that an effective fusion of the vertebrae 156, 157 may occur. If it is determined that the plate 105 is not in a position to secure the facet joints 160, 162 and the vertebrae 156, 157, the method 1600 may include, at step 1612, adjusting the position of the plate 105 so that the plate 105 is in a position to secure the facet joints 160, 162 and the vertebrae 156, 157 effectively. If, however, it is determined that the plate 105 is in a position to secure the facet joints 160, 162, and the vertebrae 156, 157, the method 1600 may include, at step 1614, further securing the first and second connection devices 135, 145 and the plate 105 in the position to secure the facet joints 160, 162 and the vertebrae 156, 157. In one embodiment, securing the first and second connection devices 135, 145 and the plate 105 may mean tightening or otherwise affixing the first and second connection devices 135, 145 to ensure rigid fixation of the vertebrae 156, 157. At step 1616, the method 1600 may include closing the incision in the patient's back after securing the first and second connection devices 135, 145 and the plate 105 to the facet joints 160162, and the vertebrae 156, 157.

Furthermore, it is important to note that the methods, devices, and kits described herein may incorporate any of the functionality, components, and/or features described herein or otherwise and are not intended to be limited to the description provided above.

The illustrations of arrangements described herein are intended to provide a general understanding of the structure of various embodiments, and they are not intended to serve as a complete description of all the elements and features of apparatuses and methods that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

I claim:

1. A method for securing facet joints of a spine of a patient, the method comprising:
   positioning a first screw directly through a first facet joint of the spine and a second screw directly through a second facet joint of the spine of the patient; and
   engaging a plate with the first and second screws after the first and second screws are positioned through the first and second facet joints, wherein the plate includes first and second slots each comprising an opening extending to an edge of the plate through which to respectively receive the first and second screws when engaging the plate after the first and second screws are positioned through the first and second facet joints, wherein the opening of the first slot is perpendicular to the opening of the second slot and the first slot is configured to extend perpendicular to a long axis of the spine of the patient.

2. The method of claim 1, wherein the plate is configured to cross a midline of the spine and cover the first and second facet joints when the plate is engaged with the first and second screws.

3. The method of claim 1, wherein the plate is configured to extend up over lamina of the spine when the plate is engaged with the first and second screws.

4. The method of claim 1, wherein the plate is configured to engage a spinous process of the spine when the plate is engaged with the first and second screws.

5. The method of claim 1, wherein the first and second screws each include a head located at distal ends of the first and second screws, wherein each head is wider than the first and second slots of the plate such that when the plate is engaged with the first and second screws, the plate is secured to the first and second screws.

6. The method of claim 1, further comprising disengaging the plate from the first and second screws.

7. The method of claim 1, wherein the first and second screws each include a head located at distal ends of the first and second screws, wherein each head is shaped such that when the plate is engaged with the first and second screws, a portion of the head of the first screw rests on a pair of indentations adjacent to the first slot and a portion of the head of the second screw rests on a pair of indentations adjacent to the second slot, wherein the pair of indentations adjacent to the first slot conform to a shape of the portion of the head of the first screw, and wherein the pair of indentations adjacent to the second slot conform to a shape of the portion of the head of the second connection device.

8. The method of claim 1, further comprising tightening the first and second screws, without removing the first and second screws from the first and second facet joints, so as to securely implant the plate onto the spine of the patient.

* * * * *